United States Patent [19]

Dickey

[11] 4,086,458
[45] Apr. 25, 1978

[54] ELECTRICAL SWITCH FOR USE BY THE DISABLED

[75] Inventor: Herbert C. Dickey, South Natick, Mass.

[73] Assignee: The Ealing Corporation, South Natick, Mass.

[21] Appl. No.: 719,929

[22] Filed: Sep. 2, 1976

[51] Int. Cl.² ............................................. H01H 3/02
[52] U.S. Cl. ................................ 200/85 R; 200/86 R
[58] Field of Search ............................ 200/85 R, 86 R

[56] References Cited

U.S. PATENT DOCUMENTS

| 2,790,873 | 4/1957 | Fleming | 200/86 R |
| 3,209,089 | 9/1965 | Weissburg | 200/86 R X |
| 3,243,540 | 3/1966 | Miller | 200/86 R |
| 3,509,360 | 4/1970 | Miller | 200/86 R X |
| 3,641,299 | 2/1972 | Mayer | 200/86 R X |
| 3,718,791 | 2/1973 | Szablowski | 200/86 R X |
| 3,722,086 | 3/1973 | Wikkerink et al. | 200/86 R X |

*Primary Examiner*—James R. Scott
*Attorney, Agent, or Firm*—Breed, Stairs & Handal

[57] ABSTRACT

A specialized switch particularly suited for use by the disabled is disclosed. The inventive switch comprises a resilient contacting assembly, having a pair of electrically conducting members, in a housing. The contacting members are maintained out of electrical contact with each other by suitable means associated with the assembly. Application of pressure to the housing brings the members into contact with each other, closing the switch.

17 Claims, 4 Drawing Figures

ELECTRICAL SWITCH FOR USE BY THE DISABLED

BACKGROUND OF THE INVENTION

With the growing use of various automated and electronic systems in hospitals, nursing homes and other institutions which include facilities for the treatment and administering of disabled individuals, there has been an increasing call for devices which allow a patient, though he may be severely handicapped, to operate such apparati as nurse calling systems, televisions, automatic reading machines and the like without the aid of another person.

In the past, a number of techniques have been utilized in order to enable severely handicapped individuals to operate such devices. For example, one widely used method involves a pneumatic arrangement for actuating a normally open or normally closed switch. In accordance with this technique, the handicapped person places a tube with a mouthpiece in his mouth and either blows or draws to displace a diaphragm sealing the other end of the tube. Movement of the diaphragm actuates a switch to achieve various control functions. However, this particular technique, though it does solve a number of problems, suffers from several disadvantages. For example, the use of a mouthpiece is far from sanitary and, in fact, makes it impossible for a machine to be used by different individuals without having an attendant change the mouthpiece. Still another disadvantage of this type of system is the rather unnatural condition which the user must maintain. Specifically, he must hold the mouthpiece in his mouth and maintain a good seal with his lips. Over extended periods of time the muscles of the jaw and lips will tend to tire, thus making use of the switch difficult and uncomfortable.

Still another technique employed to enable handicapped individuals to operate electrical equipment is the use of a pressure-operated foot switch. Suitable switches for this purpose are shown in U.S. Pat. Nos. 3,710,054, 3,715,541, 3,812,313 and 3,821,500. However, switches of this type suffer from a number of severe disadvantages. For example, a rather substantial amount of pressure is required in order to operate them. Their construction thus makes them suitable only for actuation by foot. Often, a handicapped person does not have the use of his feet and cannot use such a switch. Moreover, even if he does have the ability to move his feet he would be required to wear a shoe or similar protective covering for his feet because prolonged contact with the switch's hard surface causes irritation, discomfort and fatigue. Still another disadvantage of such switches is that they are not sanitary and serve to transmit germs from one patient to another.

SUMMARY OF THE INVENTION

In accordance with the present invention an electrical switch for use by disabled persons is provided. The invention switch may be used for extended periods of time without discomfort or pain. Moreover, when the surface becomes soiled or when it has been subjected to conditions where the communication of germs is likely, the outer covering of the switch may be easily replaced. The switch comprises a compressible housing which defines an aperture. A resilient contacting assembly comprising a pair of electrically conducting members is positioned within the aperture. Means for maintaining the members in spaced relationship to each other is provided. Electrical conductor means, having at least two electrically conducting elements, with each of the elements being electrically connected to one of the electrically conducting members, is provided to facilitate electrical connection to the apparatus with which the switch is to be used.

DETAILED DESCRIPTION OF THE PREFERRED EMBODIMENT

Figure 1:
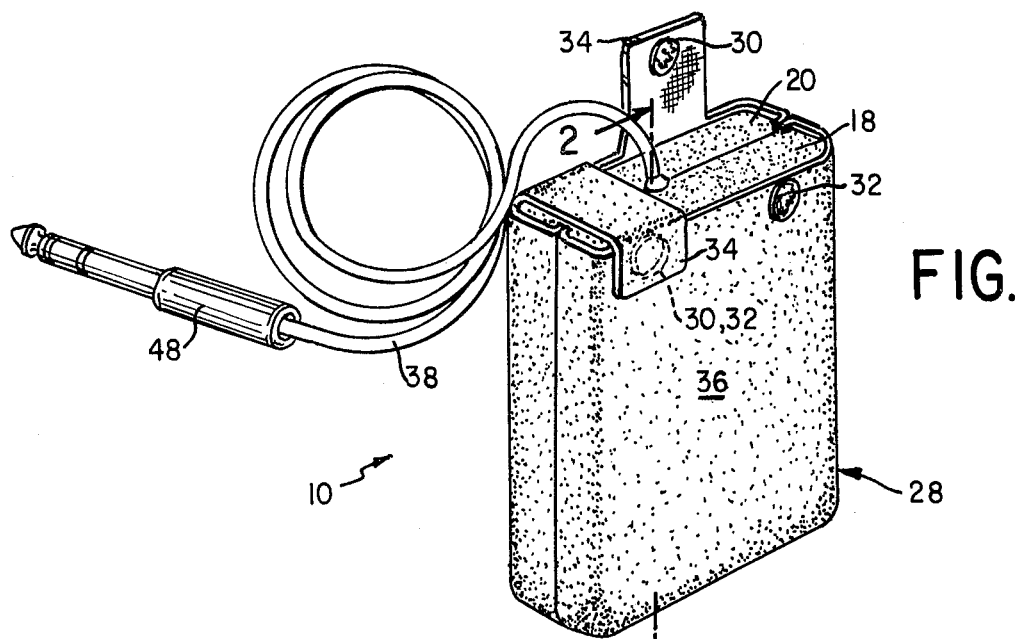
FIG. 1 is a perspective view of a switch constructed in accordance with the present invention.
Figure 2:
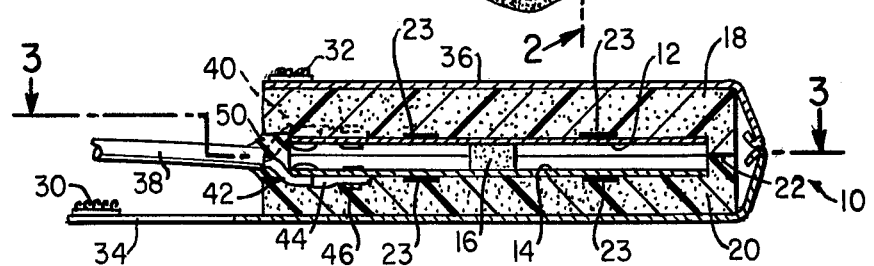
FIG. 2 is a view along lines 2—2 of FIG. 1.
Figure 3:
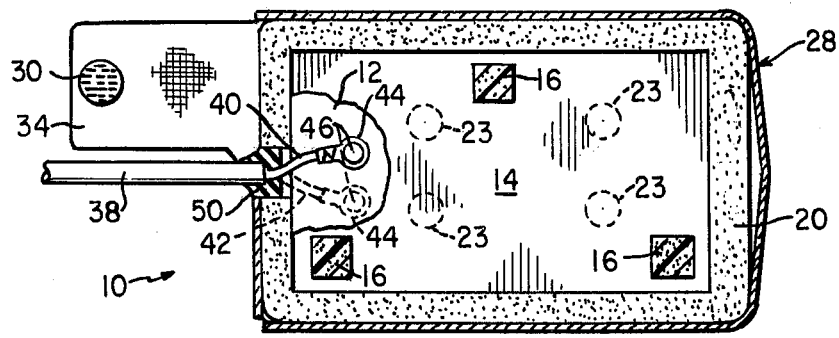
FIG. 3 is a cross-sectional view along lines 3—3 of FIG. 2.

Referring to FIGS. 1—3 a switch 10, particularly suitable for use by even a severely handicapped individual, is illustrated. Switch 10 incorporates a flexible contacting assembly comprising a pair of planar flexible contacting members 12 and 14. Contacting members 12 and 14 are positioned wthin switch 10 in facing relationship to each other. Contacting members 12 and 14 may be made of any resilient conducting material having an excellent mechanical memory. In accordance with the preferred embodiment, a full-hard or hard-hard beryllium copper sheet having a thickness of 0.004 inches has been found to give excellent results. However, any material having similar resilience and memory, such as phosphorous-bronze or plastic with a conductive layer adhering to it, will also work well.

Secured to contacting member 14 are a plurality of compressible separators 16. Separators 16 are made of polyurethane foam having a density of approximately 2 lbs/ft$^3$. Separators 16 are secured to contacting plate 14 by any suitable flexible adhesive, such as the silicone plastic adhesive marketed by Dow Corning and having the catalog designation of RTV No. 732. Separators 16 serve the purpose of preventing contacting members 12 and 14 from touching each other when the switch is in the unactuated state. However, when the switch is actuated by pressure, their compressibility together with the flexibility of the contacting plates assures a very positive switch closing action.

A soft-surfaced texture for the switch is provided by housing the contacting members within a switch housing made of polyurethane foam having a density of 2 lbs/ft$^3$. The switch housing comprises a pair of housing members 18 and 20. Housing member 18 is secured to housing member 20 by a layer 22 of silicone plastic adhesive. Contacting members 12 and 14 are thus held in facing relationship with each other within the housing of the switch by members 18 and 20. Insofar as housing members 18 and 20 are made of polyurethane foam, any forces applied to the housing will be transmitted to contacting members 12 and 14.

Switch 10 further comprises a cloth covering 28 which may be made of any soft fabric. In accordance with the present invention it has been found that natural fibers are preferable for the fabric because of their feel, absorbency and other properties, especially when subjected to prolonged contact with the human body. Velcro fastening material tabs 30 and 32 are secured to covering 28, thereby allowing flaps 34 of covering 28 to be draped around housing members 18 and 20 and secured to the main portion 36 of covering 28. Both flaps 34 are secured in this manner when the switch is in use. Fastening material tabs 30 and 32 may be secured to covering 28 in any one of a number of ways, for example by stiching, glueing or stapling.

Electrical connection to contacting members 12 and 14 is made via a cable 38 which incorporates a pair of insulated conductors 40 and 42. Conductors 40 and 42 are electrically connected to terminals 44, which in turn are secured by rivets 45 to the contacting members. Cable 38 terminates in a plug 48 which allows the switch to be connected into any electrical system. In order to protect the terminals from mechanical stresses cable 38 is mechanically joined to the housing members by a quantity 50 of silicone rubber of the same type that is used to secure separators 16 to contacting member 14 and housing members 18 and 20 to each other. As an added precaution, a quantity 52 of insulative material, such as silicone rubber adhesive, may be applied to the contacting elements as shown in the drawings. In the event that cable 38 becomes separated from housing members 18 and 20 and is twisted, bringing contacting members 12 and 14 into contact with each other, they will not be electrically connected to each other and the switch will not be falsely actuated.

The compressibility of switch 10 and the softness of the outer covering 28 allows it to be brought into contact with the human body for extended periods of time without discomfort or pain. Moreover, in the event that the covering becomes soiled, covering 28 may be removed from the other parts of the switch by separating fastening material tabs 30 from mating tabs 32 and pulling the covering while holding housing members 18 and 20. A clean fabric covering may then be put on the switch and the soiled covering washed.

Figure 4:
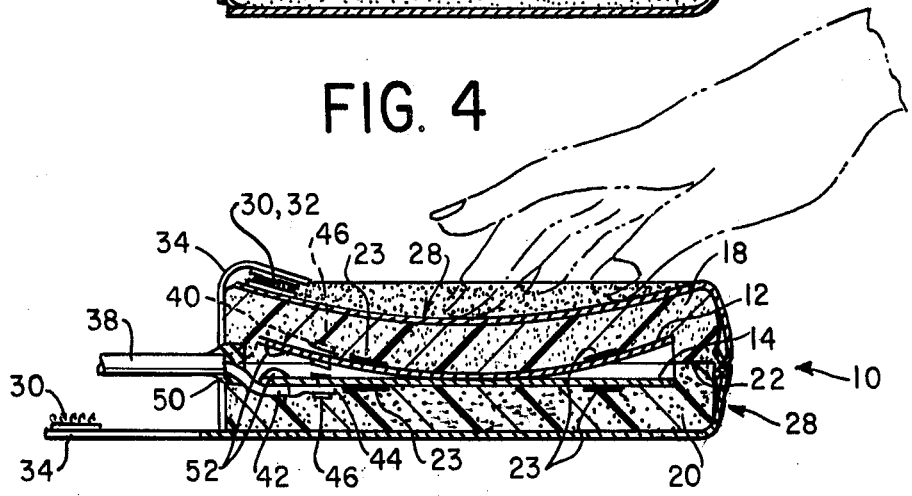
FIG. 4 is a view of the inventive switch similar to the view illustrated in FIG. 2, illustrating the inventive switch in the actuated position.

When a disabled person having a limited ability to move his extremities wishes to operate an electrical device or system, the inventive switch is attached by means of plug 48 or any other suitable electrical connected means. The switch is then put into physical contact with a part of the person's body which is capable of some movement. For example, one may position the switch on a table and place the individual's elbow over the switch. When the person wishes to actuate the machine by closing the switch he simply applies pressure to the switch. This causes contacting members 12 and 14 to assume a position such as that illustrated in FIG. 4. In this position contacting members 12 and 14 are brought into electrical contact with each other, thus shorting conductor 38 to conductor 40 and completing the electrical circuit connected to plug 48.

Because of the combined action of the resiliency and exceptional memory of contacting members 12 and 14, and the compressibility of separators 16, the application of even very small pressures to the body of the switch 10 virtually assures closing of the circuit while the removal of pressure results in the dependable opening of the circuit. This thus enables a disabled individual to conveniently, or at least relatively conveniently, operate electrical equipment without the aid of another person.

While an illustrative embodiment of the invention has been described, it is understood that various modifications in the shape, form, arrangement and number of parts will be obvious to those skilled in the art. For example, the inventive switch may be fabricated using a resilient contacting assembly comprising a flexible and a rigid contacting member. In a typical situation, such a switch would be so positioned that the rigid member would be adjacent a hard surface such as a table top and the resilient member adjacent the exposed face of the switch. In such a situation, the user's hand might be positioned over the switch when it is in use. Naturally, in such a situation, the unexposed face of the switch need not be made of a compressible material. One may also desire to modify the switch by potting the junction of the cable and the contacting assembly. Likewise, one could use a fabric covering with a drawstring feature. Such changes are within the spirit and scope of the invention, which is limited and defined only by the appended claims.

What is claimed is:

1. An electrical switch, comprising:
   (a) housing means defining an aperture, said housing means being made of a bendable material which incorporates air spaces positioned, configured and dimensioned to allow said housing means to be compressed to a smaller size;
   (b) a resilient contacting assembly positioned within said aperture, said resilient contacting assembly comprising:
      (i) a pair of planar electrically conducting contacting members at least one of which is flexible; and
      (ii) compressible means for maintaining said pair of members in spaced relationship to each other in such a position that application of a force to said housing means results in deflecting said housing means and coupling said force to said flexible contacting member, flexing said flexible contacting member and bringing the contacting members into contact with each other; and
   (c) electrical conductor means having at least two electrically conducting elements, each of said elements being electrically connected to one of said electrically conducting contacting members.

2. An electrical switch as in claim 1, wherein said means for maintaining said pair of members in spaced relationship to each other comprises an adhesive securing the planar members to the inner walls of said housing means.

3. An electrical switch as in claim 1, further comprising a cloth covering.

4. An electrical switch, comprising:
   (a) bendable housing means defining an aperture;
   (b) a resilient contacting assembly positioned within said aperture, said resilient contacting assembly comprising:
      (i) a pair of electrically conducting contacting planar members at least one of which is flexible; and
      (ii) means for maintaining said pair of members in spaced relationship to each other in such a position that application of force to said housing means results in deflecting said housing means and coupling said force to said flexible contacting member, flexing said flexible contacting member and bringing the contacting members into contact with each other;
   (c) electrical conductor means having at least two electrically conducting elements, each of said elements being electrically connected to one of said electrically conducting contacting members; and
   (d) removable and replaceable cover means secured to and disposed around said housing means.

5. An electrical switch as in claim 4, wherein said means for maintaining said pair of planar members in spaced relationship to each other are a plurality of compressible separators positioned between the planar members.

6. An electrical switch as in claim 5, wherein said means for maintaining said pair of members in spaced relationship to each other further comprises an adhesive securing the planar members to the inner walls of said housing means.

7. An electrical switch as in claim 5, wherein at least a portion of said housing means is compressible and together with said separators is made of foam plastic.

8. An electrical switch as in claim 7, wherein said foam plastic is polyurethane form having a density of about 2 lbs/ft$^3$.

9. An electrical switch as in claim 5, further comprising a quantity of insulating material adhering to that portion of one of the planar members adjacent where the conductor means meets that planar member and on the side of that planar member which faces the other planar member.

10. An electrical switch as in claim 5, wherein each of said compressible separators is secured to one of said planar members by an adhesive which is flexible after it has set.

11. An electrical switch as in claim 10, wherein both said planar members are flexible and are made of beryllium-copper.

12. An electrical switch as in claim 11, wherein said means for maintaining said pair of members in spaced relationship to each other further comprises an adhesive securing the planar members to the inner walls of said housing means.

13. An electrical switch as in claim 12, wherein said housing means incorporates said separators which are made of foam plastic.

14. An electrical switch as in claim 5, wherein all portions of said housing means are displaceable.

15. An electrical switch, comprising:
  (a) bendable housing means defining an aperture;
  (b) a resilient contacting assembly positioned within said aperture, said resilient contacting assembly comprising:
    (i) a pair of electrically conducting contacting members at least one of which is flexible; and
    (ii) a plurality of separators for maintaining said pair of members in spaced relationship to each other in such a position that application of a force to said housing means results in deflecting said housing means and coupling said force to said flexible contacting member, flexing said flexible contacting member and bringing the contacting members into contact with each other, said separators being made of a bendable material that incorporates air spaces positioned, dimensioned and configurated to make said separators compressible into a smaller volume upon the application of force to said bendable housing means; and
  (c) electrical conductor means having at least two electrically conducting elements, each of said elements being electrically connected to one of said electrically conducting contacting members.

16. An electrical switch as in claim 15, wherein at least a portion of said housing means is compressible.

17. An electrical switch, comprising:
  (a) compressible housing means defining an aperture;
  (b) a resilient contacting assembly positioned within said aperture, said resilient contacting assembly comprising:
    (i) a pair of flexible planar electrically conducting contacting members; and
    (ii) a plurality of compressible separators in spaced relationship to each other in such a position that application of a force to said housing means results in deflecting said housing means and coupling said force to at least one contacting member, flexing said flexible contacting member and bringing the contacting members into contact with each other;
  (c) electrical conductor means having at least two electrically conducting elements, each of said elements being electrically connected to one of said electrically conducting contacting members; and
  (d) removable and replaceable cover means secured to and disposed around said housing means.

* * * * *